United States Patent [19]

Fry

[11] Patent Number: 5,423,764
[45] Date of Patent: Jun. 13, 1995

[54] LAVAGE APPARATUS

[76] Inventor: William A. Fry, 11660 W. 155th Ter., Overland Park, Kans. 66221

[21] Appl. No.: 76,182

[22] Filed: Jun. 14, 1993

[51] Int. Cl.6 .................... A61M 5/00; A61M 25/00
[52] U.S. Cl. ................................... 604/187; 604/280
[58] Field of Search ............... 604/187, 239, 266, 268, 604/270, 275, 280, 283, 284

[56] References Cited

U.S. PATENT DOCUMENTS

| | | | |
|---|---|---|---|
| 3,190,290 | 6/1965 | Alley et al. | 604/280 |
| 3,288,901 | 11/1966 | Clark | 604/280 |
| 3,469,579 | 9/1969 | Hubert | 604/283 |
| 3,885,561 | 5/1975 | Cami | 604/280 |
| 4,516,970 | 5/1985 | Kaufman et al. | 604/270 |
| 4,613,323 | 9/1986 | Norton et al. | 604/270 |
| 4,661,094 | 4/1987 | Simpson | 604/280 |
| 4,698,058 | 10/1987 | Greenfeld et al. | 604/266 |
| 4,769,014 | 9/1988 | Russo | 604/270 |
| 4,790,809 | 12/1988 | Kuntz | 604/280 |
| 5,279,596 | 1/1994 | Castaneda et al. | 604/280 |

Primary Examiner—C. Fred Rosenbaum
Assistant Examiner—Frank Wilkens, III
Attorney, Agent, or Firm—Thomas M. Scofield

[57] ABSTRACT

Lavage apparatus including a tube member having a distal end portion and a proximate end, with a primary lumen extending axially through the tube member for flow communication between said distal end portion and the proximate end and secondary lumens extending through the distal end portion, the secondary lumens being mutually radially opposed and disposed at different distances from the distal end of the tube member to assure unobstructed flow and having the first secondary lumen disposed a distance D from the distal end of the tube member, and a radiopaque tip member extending a distance D into the primary lumen to avoid any internal spaces in which fluid may collect, the tip member also having a beveled shoulder for engaging, in compression, the distal end of the tube member to avoid any annular cavity or gaps in which fluid may collect, the tube member also having an elongate axial radiopaque strip intersecting at least the first secondary lumen to enable medical personnel to assure proper placement of the distal end portion.

7 Claims, 2 Drawing Sheets

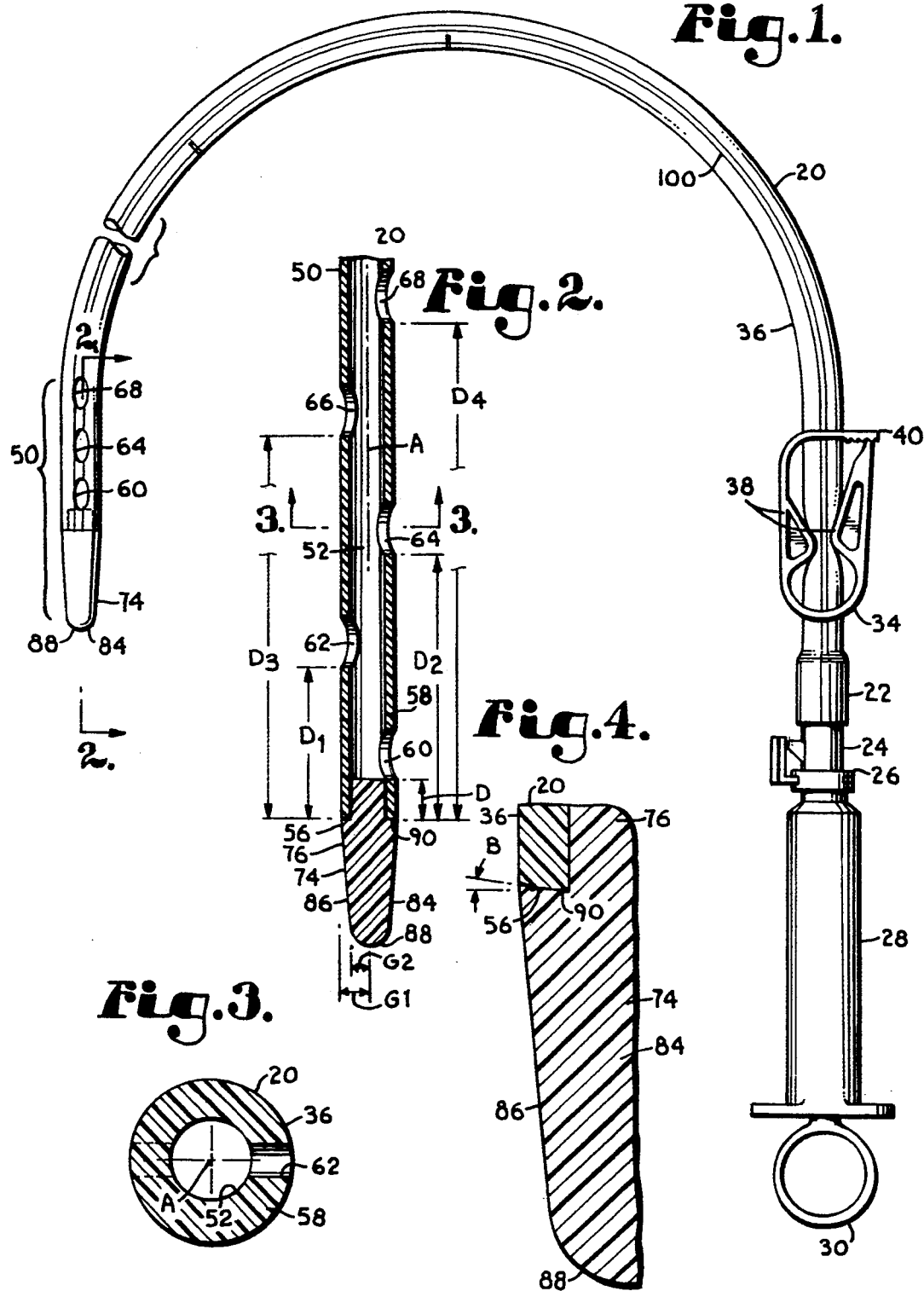

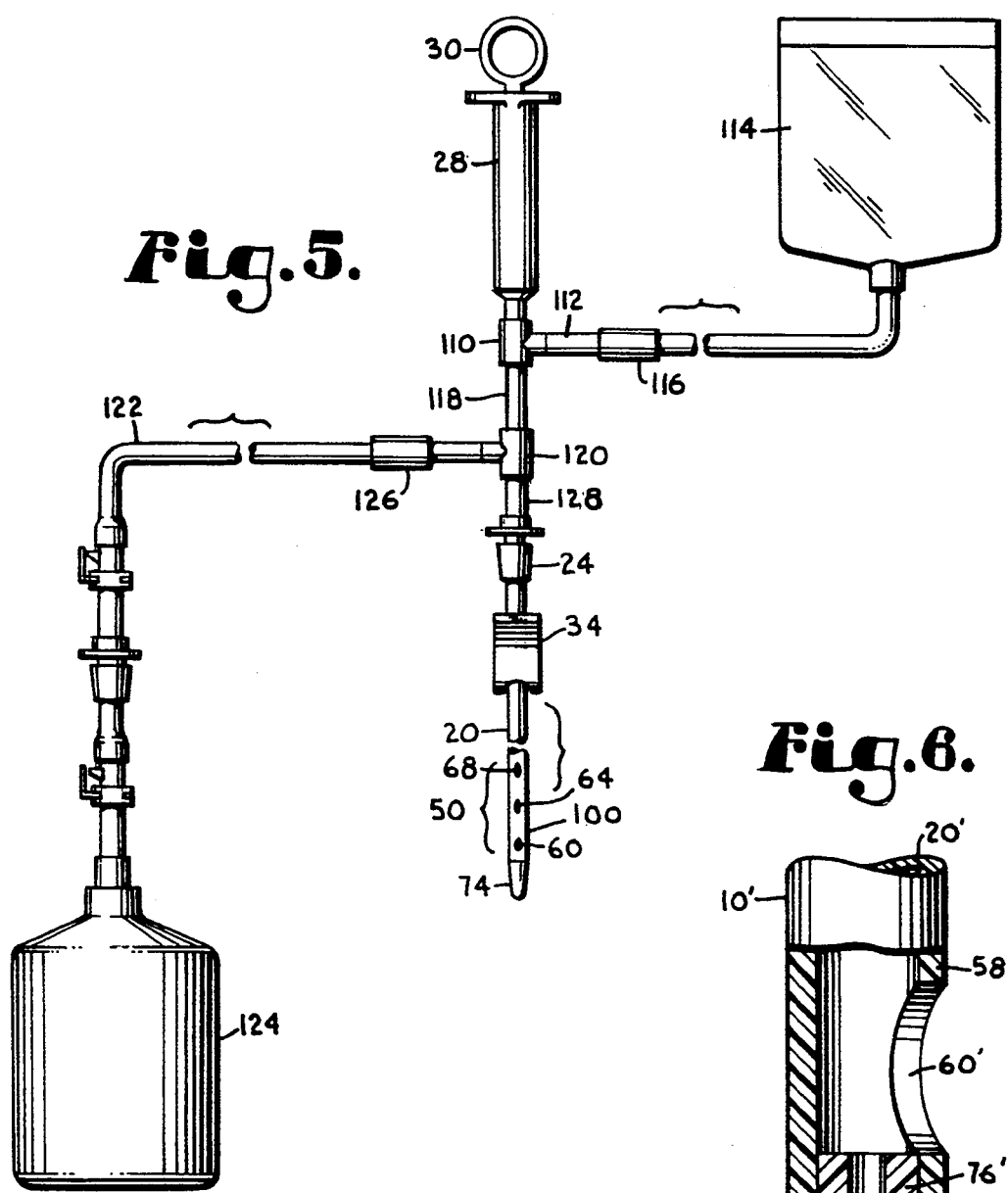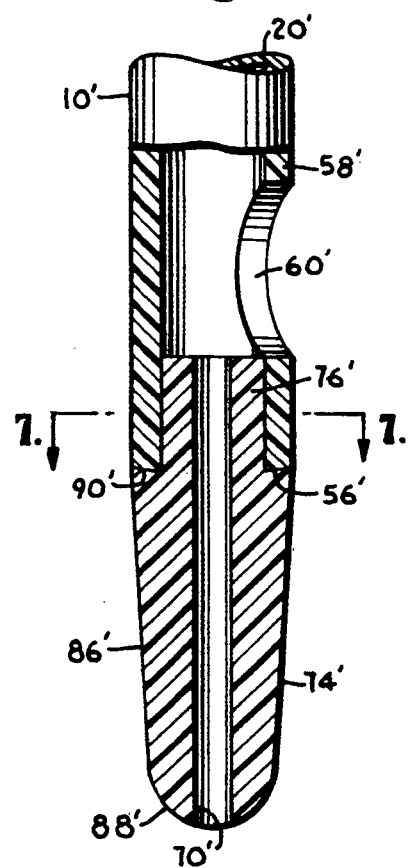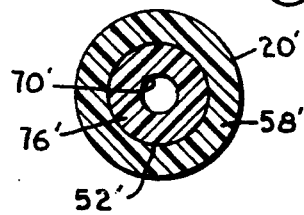

LAVAGE APPARATUS

TECHNICAL FIELD

This invention generally pertains to medical apparatus useful in lavage, catheterization and direct feeding, and more particularly to apparatus insertable into the human body through natural openings or incisions for the instillation into or aspiration of material from the natural voids found in the human body.

BACKGROUND ART

In medical practice, it is often desirable and necessary to provide means for instilling material into or aspirating material from the body of a patient. As is commonly known, hypodermic needles serve these functions adequately for those portions of the human body which are relatively solid, such as bone and muscle mass. However, the human body contains many natural voids such as the stomach and intestines, blood vessels, lungs, bladders and so forth, for which, for example, hypodermic needles are typically unsatisfactory as means for instilling or aspirating materials.

It is often necessary to cleanse these natural voids, or to remove or replace the fluid or material found therein. For example, it is not uncommon for an individual to unintentionally ingest undesirable or even toxic substances into the stomach. These substances, along with any other materials thereby contaminated, must be removed from the stomach and the stomach cleansed. This is typically accomplished by a lavage apparatus capable of instilling material and aspirating material directly to and from the stomach.

To meet the substantially higher mass flow requirements of material flow needed to medically service the natural voids of the body, apparatus including body-insertable tubes of substantially greater diameter than the typical hypodermic needle are commonly employed. These tubes are typically provided with a distal end insertable through either a natural opening in the body, such as the nasal, oral or anal opening, or insertable through an artificial opening or incision in the body. The distal end is then directed to the desired disposition in the body as required by the particular medical considerations. A proximate end of the tube remains outside the body where the medical personnel may conveniently perform the desired operations with the tube.

An axial passage or primary lumen extends through the tube member from at or near the distal end portion to the proximate end for communicating material through the lavage apparatus and thereby into and out of the body void. One or more secondary lumens intersect the primary lumen and permit material communication, through the distal end portion between the primary lumen and the concerned body void. The disposition of these lumens is most important, since the secondary lumens permit the actual material flow and obstruction thereof can inhibit or prevent the necessary material flow.

A number of difficulties have arisen in connection with the use of such tubes, however. Since the tubes are of relatively large diameter and the internal body tissues are typically relatively fragile and delicate, such a tube must present an exterior surface which is designed to minimize incidental damage to internal body tissue. Furthermore, the body cannula through which such tubes are inserted are not linear, and such a tube must be of sufficient flexibility to enable it to follow the contours of such body cannula as the esophagus or the intestines, while retaining sufficient rigidity to enable the medical personnel inserting the tube to direct the tube appropriately within the body.

It is also typically desirable to minimize the transfer of body fluids from one location in the body to another in order to minimize the risk of infection and subsequent distress to the patient. For example, if the distal end of the lavage apparatus permits the accumulation of fluids in the primary lumen or in a cavity on the exterior surface of the distal end, the accumulated fluids enable rapid reproduction of undesired bacterial or viral agents. Also, toxic or even otherwise harmless fluids so accumulated on the exterior surface of the distal end, such as those commonly found in the stomach, may enter other portions of the body in which such fluids represent a hazard, such as subcutaneous body tissues and muscle, when the lavage apparatus is removed, especially through an incision.

An additional substantial difficulty lies in the fact that the distal end of such a tube is not visible to the medical personnel after initial insertion into the body. The personnel emplacing the tube can experience great difficulty in determining the actual location of the distal end of the tube within the body. While knowledge of the exact location of the distal end of the tube is not critical in all cases, the proper disposition of the distal end is necessary in many cases to ensure that the necessary medical operations are properly completed.

A number of attempts have been made to alleviate these problems. For example, the distal end of such tubes are often provided with a tip member or other closure member to assist in properly guiding the tube. This tip member is typically designed to aid in the directing of the tube within the body. However, both the tip member and the tube are typically flexible and an annular cavity may form at the junction of the tube and the tip member, which permits the undesirable transfer of body fluids. Furthermore, the relative flexing of the tube and tip member can interfere with the bonding of the tip member to the tube, which may permit the tip member to detach within the body so as to pose a serious health risk to the patient. Some tubes are further provided with a radiopaque tip member at the distal end of a tube, which permits the medical personnel to determine the general disposition of the distal end of the tube member within the body by radiological techniques. However, internal body features appear at differing degrees of radiopaqueness and can mislead the medical personnel as to the actual placement of the distal end.

In order to overcome the problem of tip member detachment, other apparatus have been provided which include a tube member having an integrally formed tip member. This avoids the risk of detachment but prevents the use of a tip member having a flexibility different than that of the tube member and reduces the guidability of the tube member within the body. Such a solution also prevents the use of a tip member having a radiopaqueness different from the tube. Other proposed solutions have included other means of bonding the tip member to the tube to produce a one-piece assembly from the tip member and tube components. Such solutions often are substantially more expensive and time-consuming to manufacture, with the result that the tubes so produced are substantially more expensive.

It is therefore an object of the present invention to provide such a lavage apparatus as is readily guidable in the human body.

It is a further object of the present invention to provide such a lavage apparatus as will include means for permitting accurate radiopaque observation of the disposition thereof in the human body.

It is yet a further object of the present invention to provide such a lavage apparatus as will include means for permitting accurate radiopaque observation of the disposition of the secondary lumens.

It is another object of the present invention to provide such a lavage apparatus as will prevent the undesirable accumulation of fluids in or on the distal end portion thereof.

It is yet another object of the present invention to provide such a lavage apparatus as may employ a tip member having a differing degree of flexibility than that of other portions of the lavage apparatus.

It is yet another object of the present invention to provide such a lavage apparatus as having exactly marked distances from the distal tip to enable the operator to know precisely where placement may occur.

Yet another object of the invention is to have and provide a lavage tube that cooperates with a fitting that will allow both delivery and aspiration of lavage fluid or stomach contents in such a way as to prevent the lavage tube from becoming separated from the delivery device (e.g., syringe).

Yet another further object of the invention is to provide such a lavage tube working/insert end assembly, including tip, perforated tube portion and non-perforated tube portion wherein the durometer measure of the tip material, tube portion with perforations or holes therethrough and following non-perforated tube portion causes the tip and following perforated tube portion of the lavage tube to follow the greater curve of the mouth/throat rear wall whereby to avoid this tube entering the bronchial tube.

These and other objectives of the present invention will become apparent in the specification and claims that follow.

SUMMARY OF THE INVENTION

The subject invention is a lavage apparatus having a tube member including a proximate end and a distal end portion which is body insertable and a primary lumen communicating between the distal end portion and the proximate end. One or more secondary lumens are provided in the distal end portion and intersect the primary lumen to communicate through the distal end portion of the tube member, with the first secondary lumen disposed immediately adjacent the tip member. The tube member is further provided with a radiopaque stripe extending laterally along the tube member from the tip member to or near the proximate end. The radiopaque strip intersects the first secondary lumen to ensure that the first secondary lumen is radiologically visible and thus to ensure that the distal end portion is desirably emplaced in the body. The distal end portion includes a radiopaque tip member.

BRIEF DESCRIPTION OF THE DRAWINGS

FIG. 1 shows a medical device according to the present invention.

FIG. 2 shows a partial cross-sectional view of the distal end portion of the subject invention taken along section lines 2—2 of FIG. 1.

FIG. 3 shows a cross-sectional view of the subject invention taken along section lines 3—3 of FIG. 2.

FIG. 4 shows an enlarged partial cross-sectional view of the distal end portion of the subject invention as shown in FIG. 2.

FIG. 5 shows the subject invention in cooperation with a lavage operating means to provide a complete lavage system.

FIG. 6 shows an enlarged partial cross-sectional view of an alternative embodiment of the distal end of the subject invention.

FIG. 7 shows a cross-sectional view of the alternative embodiment of the distal end of the subject invention taken along section lines 7—7 of FIG. 6.

DETAILED DESCRIPTION OF THE PREFERRED EMBODIMENT

A lavage apparatus embodying the subject invention is generally disclosed in FIG. 1, and is referred to by the reference number 10. The lavage apparatus 10 preferably includes an elastomeric, flexible tube member 20 which has a proximate end 22. The proximate end 22 is fitted elastomerically over the cylindrical portion 24 of a mating adapter 26. The mating adapter 26 is removably and selectively secured to a two-way deliver or aspirate syringe or pump 28. As is known to those skilled in the art, the syringe/pump 28 is operable as a pump to act as a means for causing material flow in the lavage apparatus, whereby material such as liquid and semi-solids and other fluids may be instilled or aspirated by the lavage tube 20 and apparatus. Operation of the syringe/pump 28 is accomplished by causing linear movement of the grasp ring 30 while otherwise ensuring that the syringe/pump remains relatively stationary, as is believed known to those skilled in the relevant art.

A closure clip 34 of the commonly known type is also shown in engagement with the tube member 20 generally adjacent the proximate end 22. The closure clip 34 does not constitute part of the present invention, and will not be described in detail. However, as is generally known, the closure clip 34 is disposed about the exterior surface 36 of the tube member 20 and includes selectively moveable opposed tube engagement surfaces 38 which selectively engage in compression the tube exterior surface 36 so as to compress the tube member 20 and thereby prevent any material flow therethrough. A locking means 40 is also provided to ensure that the closure clip 34 retains the desired degree of compressive engagement with the tube exterior surface 36.

The mating adapter 24, the syringe 28 and the locking clip 34 do not comprise part of the present invention. Those skilled in the relevant art will understand that these components exemplify suitable components necessary or desirable in the lavage apparatus 10, and that other components may be readily substituted.

At the opposite end of the tube member 20 is a distal end portion 50. The distal end portion 50 is more clearly shown in FIGS. 2 through 4. As more particularly seen in FIG. 2, a primary flow passage or lumen 52 extends through the tube member 20, preferably defined about the axis A of the tube member 20 so as to ensure generally uniform wall thickness and to improve the strength and longevity of the tube member 20. The primary lumen 52 permits flow communication in the interior of the tube member 20 between the distal end portion 50 and the proximate end 22. Flow communication between the proximate end 22 and the flow causing means 28 is provided by the mating adapter 24.

The distal end portion 50 includes the distal end 56 of the tube member 20. The distal end 56 is an annular ring surface which is perpendicular to the tube axis A, having a width equal to the thickness of the tube wall 58.

A first secondary passage or lumen 60 communicates through the tube member wall 58 and provides flow communication from the primary lumen 52 to the tube exterior 36. The first secondary lumen 60 is removed from the distal end 56 by a distance D. According to the preferred embodiment, a total of five secondary lumen are provided, as follows: the first secondary lumen 60; a second secondary lumen 62, removed a distance D1 from the distal end 56; a third secondary lumen 64, removed a distance D2 from the distal end 56; a fourth secondary lumen 66, removed a distance D3 from the distal end 56; and a fifth secondary lumen 68, removed a distance D4 from the distal end 56.

According to the preferred embodiment, the first secondary lumen 60, the third secondary lumen 64 and the fifth secondary lumen 68 are linearly disposed in the distal end portion 50, and the second secondary lumen 62 and the fourth secondary lumen 66 are also linearly disposed in the distal end portion 50. The second secondary lumen 62 and the fourth secondary lumen 66 are preferably 180 degrees radially removed about the axis A from the first secondary lumen 60, the third secondary lumen 64 and the fifth secondary lumen 68, so that the secondary lumens 60, 62, 64, 66 and 68 are mutually opposed in the distal end portion 56. Furthermore, the distances D, D1, D2, D3 and D4 are preferably unique and different from each other to ensure linear separation between each of the secondary passages or lumens 60, 62,64, 66 and 68.

A tip member 74 is provided at the distal end 56. The tip member 74, although preferably one-piece, includes two distinct portions. The first portion is a mounting portion 76 which is preferably cylindrical and sized to securely fit the primary lumen 52 and elastomerically engage the distal end portion 50. In order to assure a proper and secure engagement between the mounting portion 76 and the distal end portion 50, a securing means such as an adhesive or dielectric bonding may be preferably employed, as will be understood by those skilled in the relevant arts. The mounting portion 74 extends into the primary lumen 52 a depth D, so that the interior face 78 of the mounting portion 76 is concomitant with the first secondary lumen 60.

The second portion of the tip member 74 is the guide portion 84. Preferably, the guide portion 84 is defined by a first, frusto-conical exterior surface 86 and a second, hemispherical exterior end surface 88. The frusto-conical surface 86 preferably has a relatively larger diameter G1 adjacent the distal end 56 of the tube member 20, the larger diameter G1 being substantially equal to the diameter of the tube exterior surface 36, and a relatively smaller diameter G2 at the juncture of the frusto-conical surface 86 and the hemispherical surface 88.

At the juncture of the guide portion 84 and the mounting portion 76 is a beveled shoulder 90. The beveled shoulder 90 is circularly generated about the axis A, but the beveled shoulder 90 is uniformly angled in an acute angle $\beta$ with respect to the mounting portion 76. The beveled shoulder 90 is frusto-conical with respect to the axis A of the tube member 20.

As seen most clearly in FIG. 4, the outer edge of the beveled shoulder 90, being that edge which is of diameter G1, engages the distal end 56 prior to the inner edge of the beveled shoulder 90. Both the tube member 20 and the tip member 74 are deformable and elastomeric, so that the engagement between the beveled shoulder 90 and the distal end 56 is a compressive, elastomeric engagement. The tip member 74 experiences a pre-loading of the mounting portion 76 due to the compressive engagement between the beveled shoulder 90 and the distal end 56. The compressive engagement also ensures that no annular gap or cavity will be presented between the tube exterior surface 36 and the frusto-conical surface 86.

Preferably, the tip member is rendered radiopaque by the compounding therewith of a suitable radiopaque substance such as the incorporation therein of $BASO_4$ in the amount of 10 to 15 percent of the tip member material. Similarly, a radiopaque stripe 100 of a similar radiopaque material is preferably provided on the tube member 20. The radiopaque stripe 100 extends laterally along the tube member 20 parallel to the tube axis A from the distal end 56 to at or near the proximate end 22. The radiopaque stripe 100 also may, but not preferably, intersects the first, third and fifth secondary lumens 60, 64, and 68. The width of the radiopaque stripe 100 will preferably be substantially less than the diameter of the tube member 20, so that the tip member 74 will be radiologically distinct. The stripe is preferably 90° displaced from its location seen on tube 20 in FIG. 3, so there is no stripe perforation intersection on either side of the tube.

A more complete lavage apparatus 10 is shown in FIG. 5. The operation of the lavage apparatus 10 as shown in FIG. 5 is substantially similar to the operation of the lavage apparatus shown in FIG. 1, and no separate description is believed necessary. The lavage apparatus according to FIG. 5 includes the tube member 20, mating adapter 24 and syringe 28 as heretofore described.

Additional components disclosed in FIG. 5 include an instillation fluid T or Y connector 110 attached for flow connection to the syringe 28 and to an instillation supply tube 112, which in turn is flowably connected to instillation fluid container 114. A selectively operable valve, clamp or closing device 116 is disposed in the instillation supply tube 112 for selectively permitting and preventing fluid flow from the instillation fluid container 114. A connecting tube 118 extends between the instillation fluid T or Y connector 110 and an aspiration fluid T or Y connector 120. An aspirated fluid tube 122 extends between the aspiration fluid T connector 120 and the aspirated fluid collection container 124. A second selectively operable valve, clamp, etc., 126 is disposed in the aspirated fluid tube 122 for selectively permitting and preventing fluid flow in the aspirated fluid tube 122. A second connecting tube 128 places the aspirated fluid T connector 120 in flow connection with the mating adapter 24 and thereby with the tube member 20. For purposes of this disclosure and since the valves, clamps or closing devices 116 and 126 do not constitute any part of the present invention, the valves 116 and 126 are considered manually operated.

In operation, the body of a selected patient may be radiologically illuminated. The distal end portion 50, which is the body-insertable portion of the lavage apparatus 10, is then inserted by suitable medical personnel through a suitable body opening such as the mouth of the patient. As visual contact with the distal end portion 50 is lost, the radiopaque tip member 74 and strip 100 will be illuminated radiologically so that the medical personnel can suitably guide the distal end portion 50 within the body passages, for example, through the esophagus and to the stomach. Furthermore, the exact positions of the secondary lumen 60, 64 and 68 will radiologically visible, so that the lumen 60, 62, 64, 66 and 68 may be emplaced as will best provide unobstructed flow of material through the respective lumen and into the primary lumen 52. Such may be confirmed by fluoroscopy, by the precisely marked distances or lengths on the tube 20 or other means know to the art.

After the distal end portion 50 is suitably emplaced, the first valve or clamp 116 may be opened, the second valve or clamp 126 closed and the syringe 28 suitably operated by drawing out the grasp ring 30 so as to transfer instillation fluid from the instillation fluid container 114 through the instillation supply tube 112 and into the instillation fluid T connector 110 and the syringe 28. The first valve 116 is then closed and the grasp ring 30 is operated to force instillation fluid through the respective T connectors 110 and 120, through the tubes 118 and 128 and through the mating adapter 24. The instillation fluid then flows through the primary lumen 52 from the proximate end 22 to the distal end portion 50, whereupon it is discharged forcibly through the secondary lumens 60 through 68 and into the body void (or less forcibly by injector control or gravity).

The second valve/clamp 126 and clip 34, if closed are then opened and the grasp ring 30 is withdrawn to cause a relative vacuum in the primary lumen 52 so that material within the body cavity or void will be drawn into the primary lumen 52 through the secondary lumens 60 through 68. The continuing vacuum will draw the aspirated material upward through the second supply tube 128 and to the T connector 120, whereupon gravity may cause the aspirated fluid to flow through the supply tube 122 to the collection container 124. The cycle may be repeated until the instillation material is satisfactorily instilled into the body void or until the material in the body void is suitably aspirated. Those skilled in the art will also recognize that there are other variations of the cycle described which may be employed to complete the aspiration or instillation of materials (for example, gravity).

Upon completion of the instillation or aspiration process, the distal end portion 50 may be readily withdrawn from the body of the patient. Risk of infection to the patient is substantially reduced due to the location of the first secondary lumen 60, which is juxtaposed with the mounting portion 76 to ensure that no undesired collections of fluid or materials are possible within the primary lumen 52. Likewise, the compressive engagement of the beveled shoulder 90 and the distal end 56 ensures that no cavity is presented on the exterior of the distal end portion 50 in which undesired collections of fluid may be accumulated or transferred.

According to the preferred embodiment, the tube member 20 and the tip member 74 are both formed of elastomeric compounds. However, the materials in the tube member 20 and the tip member 74 need not have identical properties, in that the tip member may be more or less flexible or stiff than the tube member 20.

An alternative embodiment of the tip member 74 is presented in FIGS. 6 and 7. For clarity of description, the reference numerals are provided with a prime ('), and those reference numerals which designate the same components, surfaces or functions will be used in the description of the alternative embodiment.

In FIGS. 6 and 7, the tip member 74' is shown provided with an end-flow secondary lumen 70'. The end-flow secondary lumen 70' is preferably an axial bore extending through the tip member 74'. As shown, the end-flow lumen 70' may be used in conjunction with a tube member 20' provided with the first secondary lumen 60'. However, those skilled in the art will recognize that the end-flow secondary lumen 70' may be used in conjunction with a tube member 20' in which no other secondary lumens are provided.

The operation of a lavage apparatus 10' including the alternative embodiment of the tip member 74' is substantially identical to that of the preferred embodiment, with the only change being that instillation or aspiration of material may occur through the end-flow secondary lumen 70' in addition to flow through the secondary lumens 60 through 68, if any are provided. No further description is therefore deemed necessary.

Strip 100 is preferably displaced ninety degrees (90°) from the drawing showing in either direction for location purposes.

From the foregoing, it will be seen that this invention is well adapted to teach all of the ends and objects hereinabove set forth together with other advantages which are obvious and which are inherent to the apparatus.

It will be understood that certain features and subcombinations are of utility and may be employed without reference to other features and subcombinations. This is contemplated by and is within the scope of the claims.

As may possible embodiments may be made of the invention without departing from the scope thereof, it is to be understood that all matter herein set forth or shown in the accompanying drawings is to be interpreted as illustrative and not in a limiting sense.

Modifications to the preferred embodiments of the subject invention will be apparent to those skilled in the art within the scope of the claims that follow:

What is claimed is:

1. A lavage apparatus comprised of:
   a means for causing material flow for alternatively instilling and aspirating material;
   a tube member having a proximate end in flow connection with said flow causing means,
   said tube member further including a body receivable distal end portion with a tip member,
   said distal end portion further including a distal end of the tube mounted on said tip member,
   said tube member further defining a primary lumen communicating between said proximate end and said distal end portion and a distal secondary lumen next said distal end portion,
   said distal secondary lumen extending through the tube member wall and intersecting said primary lumen for flow communication therewith, as well as abutting the proximal end of the tip member,
   a tip member somewhat flexible and radiopaque and having a proximal lesser diameter mounting portion and a guide portion,
   said mounting portion extending into said tube primary lumen at said distal end thereof, whereby a length of said distal end of said tube member overlies and encloses said top member mounting portion in frictional engaging fashion,
   said tip member receiving said distal end tube length end on a proximal, exterior, annular distally beveled shoulder in compressive engagement thus presenting a smooth, continuous and cavity-free distal end exterior surface of tube and tip and said beveled shoulder being distally beveled at an acute angle B with respect to said distal termination of said tip member mounting portion so as to form a frusto-conical tube member tip engagement surface, there being a plurality of secondary lumens in the wall of said tube member, each additional secondary lumen being spaced proximally away from said first distal secondary lumen located at the tip member, whereby there are two rows of secondary lumens in the wall of said tube member adjacent said tip member, but each successive lumen spaced successively away therefrom and sequentially opposed to one another in the tube member wall, the interior diameter of each secondary lumen being substantially the same as the interior diameter of the tube member, said secondary lumens being slightly oval in form with the long portion of the oval essentially aligned with the internal axis of the tube, the distal guide portion of said tip member further including a hemispherical distal endmost portion and a frusto-conical outer surface, said frusto-conical surface having a relatively small diameter adjoining said hemispherical distal end surface and a relatively larger diameter of said tube adjacent said beveled shoulder therein.

2. A device as in claim 1 wherein said tube member further includes a radiopaque strip extending longitudinally from said tube member distal end to said tube member proximate end, said radiopaque strip not intersecting any secondary lumen.

3. The lavage apparatus as in claim 2 including said tip member also being radiopaque and having said mounting portion engaging said tube member distal end and extending a depth D into said primary lumen.

4. The lavage apparatus as set forth in claim 2 wherein said radiopaque strip has a width no greater than half the outer diameter of the tube member.

5. The lavage apparatus as set forth in claim 1 wherein said mounting portion on said tip member is cylindrical save for the distal annular beveled shoulder thereof.

6. A lavage apparatus as in claim 1 wherein the distal end of the tube member and the proximal end of the tip member, as they approach one another, both being entirely clear of attachments or extensions extending inside said tube member either from the proximal end of the tip member or the tube member itself, there thus being a fully radially open distal secondary lumen in the tube member immediately at and proximal to said mounting portion proximal end, which is completely unimpeded.

7. A lavage apparatus as in claim 1 including an axial opening through said tip member whereby to permit liquid passage therethrough, this opening being of lesser internal diameter than the tube member.

* * * * *